United States Patent [19]

Buysch et al.

[11] Patent Number: 5,650,530
[45] Date of Patent: Jul. 22, 1997

[54] PROCESS FOR PREPARING 6-OXO-(6H)-DIBENZ-[C,E][1,2]-OXAPHOSPHORINS (ODOPS)

[75] Inventors: Hans-Josef Buysch; Volker Glock, both of Krefeld; Bernd Griehsel, Bottrop; Joachim Komoschinski, Köln, all of Germany

[73] Assignee: Bayer Aktiengesellschaft, Leverkusen, Germany

[21] Appl. No.: 527,234

[22] Filed: Sep. 12, 1995

[30] Foreign Application Priority Data

| Sep. 19, 1994 | [DE] | Germany | 44 33 263.7 |
| Sep. 19, 1994 | [DE] | Germany | 44 33 264.5 |
| Feb. 17, 1995 | [DE] | Germany | 195 05 353.2 |
| Feb. 17, 1995 | [DE] | Germany | 195 05 352.4 |

[51] Int. Cl.$^6$ .................................................. C07F 9/02
[52] U.S. Cl. .................................................. 558/82
[58] Field of Search .................................................. 558/82

[56] References Cited

U.S. PATENT DOCUMENTS

| 3,702,878 | 11/1972 | Saito et al. | 558/82 |
| 4,618,693 | 10/1986 | Saito et al. | 558/82 |
| 5,008,426 | 4/1991 | Kleiner et al. | 558/82 |
| 5,391,798 | 2/1995 | Kleiner | 558/82 |
| 5,481,017 | 1/1996 | Kleiner | 558/82 |

FOREIGN PATENT DOCUMENTS

| 0582957 | 2/1994 | European Pat. Off. . |
| 0632050 | 1/1995 | European Pat. Off. . |
| 2034887 | 1/1972 | Germany . |
| 2730371 | 1/1978 | Germany . |
| 1547105 | 6/1979 | United Kingdom . |

OTHER PUBLICATIONS

S.D. Pastor, et al., Phosphorous and Sulfur, vol. 31, pp. 71–76, (1987).

Chemical Abstracts, vol. 76, abstract No. 99823z, p. 471, abstract of DE 2,034,887, (1972).

Chemical Abstracts, vol. 121, abstract No. 256037p, abstract of JP 06,145,182, p. 1198, (1994).

*Primary Examiner*—Johann Richter
*Assistant Examiner*—Laura R. Cross
*Attorney, Agent, or Firm*—Sprung Horn Kramer & Woods

[57] ABSTRACT

Optionally substituted ODOP is obtained by reaction of optionally substituted o-phenylphenol with $PCl_3$ in the presence of Lewis acids at elevated temperature in a first stage, with according to the invention an excess of at least 0.05 mol of $PCl_3$ per mol of o-phenylphenol being maintained during the entire reaction time, and, after removal of the $PCl_3$, by hydrolysis in a second stage using 1–2 mol of $H_2O$ per chlorine equivalent of the product of the first stage at 50°–150° C. and with removal of HCl and residual $H_2O$.

16 Claims, No Drawings

PROCESS FOR PREPARING 6-OXO-(6H)-DIBENZ-[C,E][1,2]-OXAPHOSPHORINS (ODOPS)

BACKGROUND OF THE INVENTION

1. Field of the Invention

The invention relates to a process for preparing optionally substituted ODOP by reaction of optionally substituted o-phenylphenols with $PCl_3$ in a first stage and hydrolysis of the product of the first stage in a second stage.

ODOPs are important additives for polymers for protection against oxidative degradation and for flame-proofing and further serve as starting materials for preparing further polymer additives.

2. Description of the Related Art

German Offenlegungsschrift 20 34 887, Example 5 and 6) discloses the preparation of 6-oxo-(6H)-dibenz-[c,e][1,2]-oxaphosphorins (ODOPs) by alkaline saponification of 6-chloro-(6H)-dibenz-[c,e][1,2]-oxaphosphorins with soda solution. In a cumbersome operation, this gives first the sodium salt of hydroxydiphenylphosphinic acid (III) in strongly contaminated aqueous-alkaline solution which has to be purified by means of activated carbon.

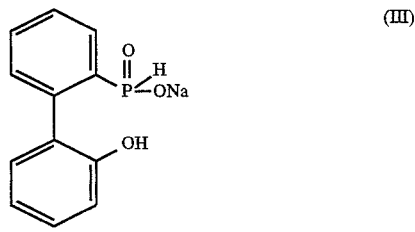

(III)

The sodium salt is convened by acidification into the free acid. This can, since it is sparingly soluble, be isolated from the aqueous salt solution. Subsequently, it has to be converted into the desired ODOP by healing to relatively high temperatures in vacuo. This is a very complicated and relatively environmentally unfriendly process, since it is associated with formation of salts and large amounts of wastewater.

Another reference (German Offenlegungsschrift 27 30 371, pp. 18 and 19) describes that 6-chloro-(6H)-dibenzoxaphosphorin at 130° C. is combined with a large amount of water, the hydrolysis is carded out, the water is distilled off under reduced pressure and the 6-oxo-dibenzoxaphosphorin is then obtained. The operation described is technically very problematical and can hardly be carried out on a large scale, since water vaporizes at 130° C. and cools the reaction mixture. It is therefore necessary to work under increased pressure if the temperature of 130° C. is to be maintained and thus uncontrolled crystallization is to be prevented, since the target compound melts significantly above the boiling point of water.

According to a further example (Example 3 in German Offenlegungsschrift 20 34 887), a crude product from the esterification of an o-phenylphenol with $PCl_3$ is hydrolyzed by pouring onto ice. This gives the corresponding phosphinic acid which has to be separated from the water and, in a separate process step, be converted into the corresponding oxaphosphorin.

The processes mentioned give, as byproduct of the oxaphosphorin synthesis, dilute and contaminated hydrochloric acid as a byproduct which is difficult to use and to dispose of as well as salt solutions and wastewater.

None of the described processes for preparing ODOP makes any statements about the yield and the purity of the product. In each case it is only established that the desired product has been obtained.

Not once is it established whether the hydrolysis proceeds smoothly and uniformly or whether it is adversely affected by side-reactions or subsequent reactions. Comparison of the process proposals discussed brings those skilled in the art to the conclusion that obviously only the alkaline saponification leads to a pure material, since only here are a melting point and a matching phosphorus analysis presented. However, this conclusion is also based on the fact that the saponification proceeds via a plurality of process steps, namely the alkaline saponification, treatment with activated carbon, filtration, precipitation with hydrochloric acid, filtration with suction, washing with water, recrystallization of the isolated phosphinic acid from ethanol/water mixture and finally the ring closure to give the oxaphosphorin by dehydration at 150° C./30 tort, associated with purification effects.

If the proposed processes are repeated, the yields and purities of ODOP found are not reproducible. In particular, the contamination of ODOP with o-phenylphenol fluctuates very widely and forces an additional purification of the ODOP obtained for it to be available in uniform quality. Our own studies indicated that the manner in which the o-phenylphenols are reacted with $PCl_3$ has a great influence on the yield and purity of the ODOP.

For the reaction of o-phenylphenols with $PCl_3$ too, there are various proposals.

According to German Offenlegungsschrift 20 34 887, $PCl_3$ and o-phenylphenols are reacted with one another in stoichiometric amounts (p. 8, last section), i.e. a deficiency or excess should be avoided if possible, if only for different reasons.

However, in Example 1 of the abovementioned German Offenlegungsschrift, 1.2 mol of o-phenylphenol is reacted with an excess of $PCl_3$, namely 1.5 mol. This is based on the escape of $PCl_3$ together with the HCl eliminated. It is calculated that the specified excess of $PCl_3$ is in actual fact carried out together with HCl during the reaction, i.e. a stoichiometric ratio of 1 mol of $PCl_3$ to I mol of o-phenylphenol is finally present.

The yield of 6-chloro-(6H)-dibenz-[c,e][1,2]-oxaphosphorin (CDOP) formed here is not indicated. Repeating the reaction gives a yield of about 80% of the theoretical yield based on o-phenylphenol. This is confirmed by the studies in Phosphorus and Sulphur, Vol. 31, 71–76 (1987), particularly p. 74 (1). In that reference, a yield of 79% of the theoretical yield is given for the synthesis of ODOP according to German Offenlegungsschrift 20 34 887.

German Offenlegungsschrift 2 730 371 describes, in Example 1 (p. 18), a reaction of o-phenylphenol (40 mol) with phosphorus trichloride (47 mol) where, unlike Example 1 of German Offenlegungsschrift 20 34 887, the Lewis acid (here $ZnCl_2$) is added from the beginning rather than only after the esterification of the o-phenylphenols with $PCl_3$. Furthermore, $PCl_3$ is added dropwise to the initially charged o-phenylphenol heated to 80° and the mixture is then brought to 180°. The further description of the experiment is imprecise and there is no indication of yield.

In EP 582 957, as in German Offenlegungsschrift 2 730 371, the catalyst is added to the reaction mixture right at the beginning and $PCl_3$ is added dropwise, but the temperature is brought immediately to 180° C. This gives a very good yield of CDOP.

In considering this prior art, those skilled in the art come to the conclusion that the combination of the proposals of German Offenlegungsschrift 2 730 371 and EP 582 957, namely the presence of the catalyst from the beginning of the reaction, the dropwise addition of PCl₃ and the setting of a high temperature over the entire reaction time, effects the yield improvement found.

Experiments carried out observing these conditions give different yields depending on other important parameters, e.g. rate at which the PCl₃ is added dropwise, rate at which the hydrogen chloride is given off and the temperature of the cooling medium in the reflux condenser. These parameters influence the amount of the PCl₃ carried out with the hydrogen chloride.

SUMMARY OF THE INVENTION

It has now been found that a reaction product of o-phenylphenols and PCl₃ suitable for the synthesis of ODOP is obtained by hydrolysis if the reaction is not carried out using a stoichiometric amount of PCl₃, as taught by German Offenlegungsschrift 2 034 887, but if an excess of at least 0.05 mol of unreacted PCl₃ per mol of o-phenylphenol used is maintained in the reaction mixture during the reaction time and particularly to the end thereof. According to these findings, an excess of PCl₃ is not sufficient but rather it has to exceed a minimum amount and has to be maintained during the entire reaction time until the end.

Distillation of such reaction mixtures gives distillates which give reproducibly high yields of pure ODOP in the subsequent hydrolysis.

Furthermore, it has been found that the hydrolysis of CDOP can be carried out using virtually the stoichiometrically required amount of water without deterioration of conversion and product purity if the distillate is allowed to react hydrolytically as melt or dissolved in an appropriate amount of a suitable solvent with the water in liquid or vapour form, generally at elevated temperature, and the hydrogen chloride formed is removed as gas or as hydrochloric acid. The ODOP thus obtained is so pure that for many purposes it can be, after removal of solvent or residual water or hydrogen chloride, crystallized from the melt and packed. It is also possible to carry out a crystallization from the solvent, should this be necessary. This represents a significant simplification of the entire process and eliminates environmental problems.

The present invention provides a process for preparing 6-oxo-(6H)-dibenz-[c,e][1,2]-oxaphosphorins (ODOPs) of the formula

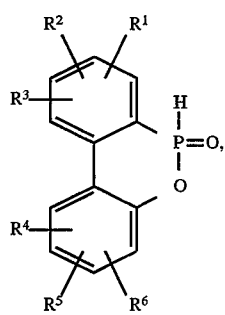

where

R¹ to R⁶ are identical or different and are hydrogen, halogen, C₁–C₄-alkyl or C₁–C₄-alkoxy, by reaction of o-phenylphenols of the formula

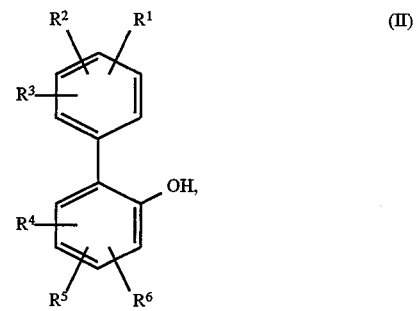

where

R¹ to R⁶ are as defined above, with phosphorus trichloride in the presence of Lewis acids with elimination of hydrogen chloride at elevated temperature in the range from 70° to 220° C. in a first stage and hydrolysis of the product of the first stage in a second stage, which is characterized in that during the entire reaction time of the first stage an amount of unreacted phosphorus trichloride of at least 0.05 mol per mol of o-phenylphenols used is maintained in the reaction mixture and the product of the first stage is, after removal of the excess PCl₃, reacted as melt or dissolved in an inert solvent with from 1 to 2, preferably from 1 to 1.7, particularly preferably from 1 to 1.5, mol of H₂O per chlorine equivalent of the product of the first stage at from 50° to 150° C., preferably at from 70 to 130° C., and HCl and residual H₂O are removed by heating to from 140° to 170° C.

DETAILED DESCRIPTION OF THE INVENTION

The present invention accordingly proceeds via the 6-chloro-(6H)-dibenz-[c,e]-[1,2]-oxaphosphorins (CDOPs) of the formula

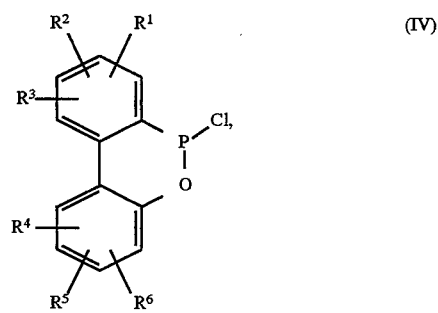

formed in the first stage, where R¹ to R⁶ are as defined above.

Suitable starting materials for the process of the invention are, on the one hand o-phenylphenols of the formula (I), where R¹ to R⁶ are, independently of one another, hydrogen, methyl, ethyl, propyl, isopropyl, butyl, isobutyl, methoxy, ethoxy, propoxy, isopropoxy, butoxy or isobutoxy, or fluorine, chlorine or bromine, preferably chlorine, and, on the other hand, phosphorus trichloride.

Catalysts are Lewis acids as are mentioned, for example, in German Offenlegungsschrift 2 034 887, preferably FeCl₃ and ZnCl₂.

Preference is given to using o-phenylphenols in which two of the radicals R¹ to R⁶ are hydrogen; particularly preferably four of the radicals R¹ to R⁶ are hydrogen; very particular preference is given to o-phenylphenol.

In each case, (II) has hydrogen in at least one of the positions of the benzene ring not substituted by OH necessary for the formation of the oxaphosphorin ring.

In the first stage, the reaction obviously proceeds by two reaction phases. In the first phase, an open-chain structure is formed with elimination of 1 mol of HCl, for which German Offenlegungsschrift 20 34 887, Example 1, formulates an esterlike structure on the OH group of the o-phenylphenol, which open-chain structure is converted, in a second reaction phase, into the cyclic structure of the oxaphosphorin ring, again with elimination of HCl; the two reaction phases can apparently partly overlap. This can be shown as follows for the example of the unsubstituted o-phenylphenol:

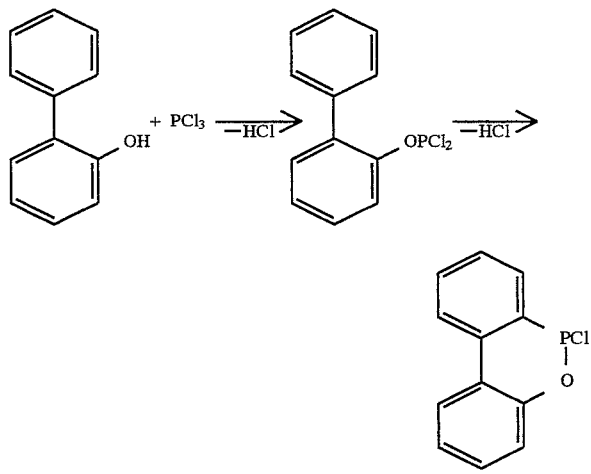

The hydrolysis in the second stage apparently proceeds as follows:

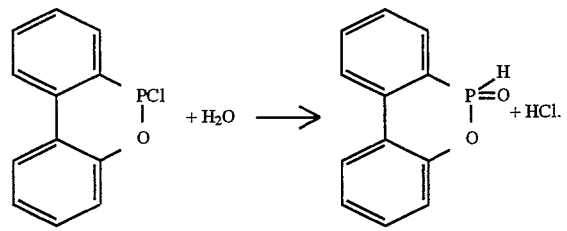

The essential feature of the present invention is the continual maintenance of a molar excess of at least 0.05 mol of unreacted $PC_3$ per mol of o-phenylphenol in the first stage, combined with the hydrolysis described in detail further below.

This could not be deduced from the current prior art. This method reliably and reproducibly gives high yields, indeed independently of whether the catalyst is added right at the beginning or only after the esterification, the entire amount of $PCl_3$ is added right at the beginning, partly at the beginning and partly later or even metered in over the entire reaction time and of whether the reaction is carried out at low (from 70° to 140° C.) or high (180° C.) temperature at the beginning or at from 160° to 180° C. or even up to 220° C. during the ring closure.

The excess of as yet unreacted $PCl_3$ per mol of o-phenylphenol used is thus at least 0.05, preferably 0.08, particularly preferably 0.1, very particularly preferably at least 0.13, mol at every point in time of the reaction in the first stage. Larger excesses are possible, but economically limited. Thus, the excess is from 0.05 to 10 mol, preferably from 0.08 to 2 mol, particularly preferably from 0.1 to 0.5 mol, per mol of o-phenylphenol. Regardless of this excess, one mol of $PCl_3$/mol of o-phenylphenol has to be metered in for the reaction in each case.

The excess $PCl_3$ is generally removed by distillation. Subsequent reactions of CDOP are sensitive to interference by residual $PCl_3$, for example in the hydrolysis. For this reason, the distillation has to be carried out in vacuo. This in turn makes it more difficult to condense and recover the excess $PCl_3$ and its destruction in the waste gas stream requires additional effort.

It has now additionally been found that addition of a small amount of an inert solvent which has a boiling point higher than that of $PCl_3$ and lower than that of CDOP and can easily be removed by distillation enables a simple and complete removal of $PCl_3$ just by distillation at atmospheric pressure and moderate temperatures and allows reuse of the excess $PCl_3$ The total amounts of $PCl_3$ and o-phenylphenols can be added at the beginning of the reaction. It is also possible to charge one of the two starting components at the beginning and to meter in the other. The esterification of o-phenylphenol with $PCl_3$ can be carried out in a first step at the outset in the absence of the catalyst at relatively low temperatures or else in the presence of the catalyst at higher temperatures, with the ring closure reaction to give CDOP also being able to proceed simultaneously.

For the purposes of the present invention, inert solvents for the distillative removal of $PCl_3$ are those which do not react with the other materials used under the conditions used. The boiling points should be advantageously between about 90° and 200°, preferably between 100° and 180°, particularly preferably from 105° to 170°.

Suitable solvents are, for example aliphatic, aromatic and araliphatic hydrocarbons and their halogen compounds. Mention may be made of methylcyclohexane, isooctane, isodecane, isododecane, isononane, dimethylcyclohexane, benzines such as petroleum ether, dicyclopentane, decalin, toluene, cumene, xylenes, mesitylene, cymenes, chlorobenzene, chlorotoluene, bromobenzene, dichlorobenzene, chloro-cumene, ethylbenzene and diethylbenzene and mixtures of a plurality of these.

During the entire reaction time, a certain level of unreacted $PCl_3$ has to be maintained. This is at least 0.05 mol per mol of o-phenylphenol used. The minimum amount of as yet unreacted $PCl_3$ has to be maintained by metering in further amounts to the degree to which $PCl_3$ present is reacted. Of course, it is also possible for significantly more $PCl_3$ to be present in the reaction mixture. It is thus possible for the total amount of $PCl_3$ necessary for one batch, including the amounts which are additionally provided to take account of the $PCl_3$ carried out by the HCl stream, to be initially charged and o-phenylphenol to be introduced into this. This monitoring of the $PCl_3$ content then has to concentrate particularly on the end of the reaction time, because it is just then that there is a danger of going below the minimum amount.

If o-phenylphenol is initially charged, the $PCl_3$ content has to be monitored during the entire reaction time.

This can be carded out, for example, by gas-chromatographic determination of the $PCl_3$ content of the off-gas or in the reaction mixture or by other suitable methods. However, if the apparatus and reaction conditions used have been sufficiently accurately designed and matched and the losses of $PCl_3$ via the HCl stream are thus known, monitoring of $PCl_3$ at the end of the reaction can suffice.

For industrial implementation, there can be provided, for example, a sufficiently rated reflux condenser for the $PCl_3$, which boils at about 75° C., which condenser can be additionally supplied with coolant having a sufficiently low temperature. Furthermore, controlled addition of the reactants and the increase in temperature can slow down the HCl evolution and thus the velocity of the HCl given off whereby $PCl_3$ losses are kept within bounds.

The reaction can be carried out at temperatures from about 80° for the esterification up to about 220° for the ring closure. If the desired minimum content of $PCl_3$ in the reaction mixture cannot be maintained at the high temperatures, this can be achieved by slightly increasing the pressure. Furthermore, the loss of $PCl_3$ can also be significantly reduced during the entire reaction time by carrying out the reaction under pressure, for instance at 1–15 bar, preferably at 1–10 bar.

The hydrolysis in the second stage of the process of the invention is carried out using the product of the first stage as melt or solution in an inert solvent. Solvents for this purpose can be the same ones mentioned above for the removal of the $PCl_3$. Hydrolysis is preferably carried out in the solution of the same solvent which was used for $PCl_3$ removal.

It is advantageous to purify the product of the first stage prior to the hydrolysis, for example by crystallization or vacuum distillation.

The distillation of the reaction product of the first stage is carried out under reduced pressure, e.g. at from 0.01 to 50 mbar, preferably at from 0.5 to 30 mbar, advantageously in a flash evaporator such as a falling-film or thin-film evaporator or in similar apparatus known to those skilled in the art.

The amount of water required for complete hydrolysis is the stoichiometric amount, i.e. at least 1 mol of water has to be used per chlorine equivalent in the product of the first stage. The range for the amount of water to be used according to the invention is 1–2 mol, preferably 1–1.7 mol, particularly preferably 1–1.5 mol, of water per chlorine equivalent.

The hydrolysis can be carried out by dissolving the product of the first stage in one of the abovementioned solvents, with the amount of solvent advantageously being from 0.1 to 4 times the weight of the product of the first stage, and introducing the water in liquid or vapour form into the stirred solution at such a rate that the stream of hydrogen chloride given off remains manageable. For mixing the solution with the water, use can be made of stirred vessels, circulating pumps, centrifugal pumps, mixing sections having static mixers or countercurrent columns or other suitable equipment known to those skilled in the art. The hydrolysis is generally carried out under atmospheric or slightly increased pressure up to about 3 bar. However, the use of higher pressures is also possible.

Working in solvents gives a relatively free choice of reaction temperature, since the crystallization point is influenced by the mount of solvent. Thus, the temperature can vary between 50° and 150° C. It is advantageously between 70 and 130° C. At the end it is brought to from 140°to 170° C. to remove traces of HCl and water.

After this, ODOP can be allowed to crystallize from the solvent and it can then be isolated in very pure form in conventional ways. This is advantageous, for example, if the product has to meet specific purity requirements. However, the solvent can generally be removed by distillation, finally in vacuo, to a liquid-phase temperature of from about 170°to 180° C. and the resulting ODOP melt can be crystallized and packed. These two steps can be carried out, for example, by use of cooling conveyors, cooling rollers or crystallization screws or other suitable apparatus.

The hydrolysis can also be carried out directly in the melt without addition of solvents. A narrower temperature range is required here. The reaction can commence at from about 90° to 95° C. At the end of the reaction, the temperature should be at least 120° C. if uncontrolled crystallization is to be avoided. The water necessary for the hydrolysis is, owing to the relatively high temperatures, advantageously added as steam, e.g. at the bottom of the reaction vessel, with, as described above, it also being possible to use other suitable apparatus for this purpose. Here, working under slightly superatmospheric pressure would also be a possibility. The subsequent reaction procedure is as in the case where solvent is used with the obvious exception that crystallization from a solvent is only possible after the addition thereof.

EXAMPLE 1

1267 g (7.45 mol) of o-phenylphenol were placed in a three-neck flask fitted with stirrer, thermometer, high-efficiency condenser and dropping funnel and 1350 g (9.78 mol) of phosphorus trichloride were added dropwise over a period of 4 hours at about 80° C. under nitrogen and while stirring, with hydrogen chloride being eliminated. The amount of $PCl_3$ added dropwise comprised the amount of $PCl_3$ consumed by reaction per unit time and an excess of at least 52 g of $PCl_3$ (=0.38 mol=0.051 mol per mol of o-phenylphenol). Monitoring was carried out by gas chromatography or by distillative work-up of samples taken. The condenser was supplied with a powerful stream of water at from 13° to 15°. During the subsequent 6 hours, the reaction temperature was slowly and steadily increased from 80° to about 142° C. After this, 245 g of $PCl_3$ (=0.24 mol per mol of o-phenylphenol) remained in the flask and the HCl evolution ceased.

After addition of 6.4 g of zinc chloride, the temperature was steadily raised over a period of 13 hours to about 200°, until no more HCl was evolved. After this, 133 g of $PCl_3$ (=0.13 mol per mol of o-phenylphenol used) still remained in the reaction mixture. The excess $PCl_3$ was, after addition of 200 g of xylene, distilled off via a short column and collected separately; it was able to be reused in subsequent batches. The last traces of $PCl_3$ went over with a little xylene which was likewise able to be reused later. The xylene-containing mixture obtained can be subjected to further reactions. It was divided in two and one half was distilled in vacuo for the purpose of isolating pure 6-chloro-(6H)-dibenz-[c,e][1,2]-oxaphosphorin (CDOP). At a temperature at the top of from 160° to 165° C. and from 2 to 3 mbar, 838 g (>95% of the theoretical yield) of a water-white distillate having a CDOP content of 98.8% went over after an initial xylene fraction.

EXAMPLE 2 (comparative)

Example 1 was repeated, but the condenser was supplied with water at from 17 to 20°. After the first reaction phase, i.e. before the addition of zinc chloride, the reaction mixture still contained 0.14 mol of $PCl_3$ per mol of o-phenylphenol. After the addition of zinc chloride and the second reaction phase, only 0.03 mol of $PCl_3$ per mol of o-phenylphenol still remained in the flask at the end. The distillation of the crude product gives a yield of CDOP of 78% of the theoretical yield.

EXAMPLE 3 (comparative)

If the excess $PCl_3$ was removed from the mixture of the first reaction phase according to Example 2 by vacuum distillation up to a liquid-phase temperature of 140° C. prior to the addition of zinc chloride, zinc chloride was then added and the mixture was heated steadily over a period of 13 hours to 200° as in Example 1, a yield of CDOP of 61% of the theoretical yield was obtained.

EXAMPLE 4 (comparative)

816 g (4.8 mol) of o-phenylphenol and 824 g (6.0 mol) of phosphorus trichloride were slowly heated to 55° C. under nitrogen and while stirring, with elimination of HCl slowly taking place. Further heating accelerated the evolution of HCl; $PCl_3$ here boiled under reflux. After about 5 hours, the internal temperature was about 142° C. and the evolution of HCl ceased. At this time the excess of unreacted $PCl_3$ based on o-phenylphenol used was 0.14 mol per mol of o-phenylphenol, from originally 0.25 mol. 4.3 g of $ZnCl_2$ were then added and the temperature was steadily raised over a period of 10 hours to 195°, until hydrogen chloride was no longer given off. 0.03 mol of excess $PCl_3$ per mol of o-phenylphenol were then still present. The yield of CDOP was 78% of the theoretical yield.

EXAMPLE 5

1045 g (7.61 mol) of phosphorus trichloride were added dropwise over a period of 5½ hours to a mixture of 1267 g (7.45 mol) of o-phenylphenol and 6.4 g of zinc chloride, with the hydrogen chloride given off being passed through a highefficiency condenser supplied with water at 12° and then through a cold trap cooled with dry ice. During this time the temperature was from 160° to 166° and $PCl_3$ boiled under reflux.

A further 360 g of $PCl_3$ were then added dropwise at from 165° to 168° and the mixture was maintained under reflux, with HCl evolution, for 12 hours. The clearly recognizable reflux indicated a sufficient excess of $PCl_3$, which was confirmed by means of samples taken and was able to serve as a guideline in repetitions of the experiments. The final temperature was from 168° to 169° C. About 300 g of xylene were then added and a total of about 168 g of $PCl_3$, first alone and then with part of the xylene, were distilled off. About 190 g of $PCl_3$ were then present in the cold trap, so that a total of about 1215 g of $PCl_3$ were consumed. Theoretically, it should have been 1023 g, so that about 192 g were lost in the HCl stream and as a result of evaporation processes during transfer and condensation.

From the amount of about 190 g of $PCl_3$ (contents of the cold trap) which was still present in the mixture at the end of the reaction, it can be calculated that the excess of $PCl_3$ was 0.186 mol per mol of o-phenylphenol used at the point in time at which the evolution of HCl ceased.

The solution of the reaction mixture in xylene obtained after distilling off the $PCl_3$ was evaporated in vacuo and the reaction product was distilled in a high vacuum (from 159° to 163° at from 0.3 to 0.4 mbar).

This gave a water-white distillate of 1719 g (98% of the theoretical yield) and a brown resinous residue of 30 g.

EXAMPLE 6

Example 1 was repeated in an identical manner up to the distillation of the last traces of $PCl_3$ together with a little xylene.

The distillation residue was distilled at a temperature at the top of from 160° to 165° and from 2 to 3 mbar. After a small initial fraction of xylene, 1675 g of product went over, corresponding to a distillation yield of >95%.

The distillate obtained was dissolved in an approximately equal amount of xylene and admixed dropwise under vigorous stirring at 80° C. over a period of 3 hours with 131.1 g (7.29 mol) of $H_2O$, about 2.5 g more than the stoichiometrically required mount, and HCl was eliminated. After the main amount of HCl had been driven off, the temperature was increased until the mixture boiled under reflux, which was maintained for about 2 hours. The solution was then divided in two.

EXAMPLE 6a)

Part 1 of the solution obtained in Example 1 was crystallized under cooling by boiling at slowly falling pressure. The colourless crystal slurry was filtered with suction, washed with xylene and dried. This gave 685 g of a white crystal powder having an ODOP content of 99.9%, an o-phenylphenol content of 0.01% and a chlorine content of 50 ppm.

The mother liquor still contained about 93 g of ODOP and is to be used for further crystallization batches.

EXAMPLE 6b)

Part 2 of the solution obtained in Example 1 was freed of solvents in vacuo up to about 170° C. and then crystallized as melt in a small screw. This gave 760 g of a white, granulated product having an ODOP content of 99.7%, an o-phenylphenol content of 0.26% and a chlorine content of 250 ppm.

EXAMPLE 7a)

Of the distillate obtained in Example 5, 868.1 g (corresponding to 3.7 chlorine equivalents) were dissolved in 400 g of xylene and admixed dropwise at 80° C. while stirring vigorously with 65.4 g (3.63 mol) of water over a period of 2 hours, with vigorous HCl evolution taking place. After a total of 3 hours, the temperature had risen to from 135° to 140° C. and the formation of HCl had become very small. The chlorine content of the solution was 0.35%. A further 4.1 g (0.23 mol) of water were then added dropwise and the hydrolysis was completed in a further 3–4 hours.

After distilling off the xylene in vacuo to a liquid-phase temperature of from 170° to 180° C. while passing in $N_2$ gas, there remained a virtually colourless melt which was filtered through a pressure filter to remove turbidity, giving a clear melt which was crystallized in a crystallization screw.

| | |
|---|---|
| Yield: | 794.8 g, namely 98.0% of the theoretical yield, based on o-phenylphenol used |
| Hazen colour No.: | 10 (10% strength solution in acetone) |
| Content of: | |
| Chlorine: | 50 ppm |
| ODOP: | 99.8% |
| o-phenylphenol: | 0.06% |

EXAMPLE 7b)

Another part of the distillate from Example 5 was dissolved in an approximately equal amount of xylene and hydrolyzed as in Example 7a. The hot solution obtained was filtered to remove a slight turbidity and then crystallized while stirring with cooling by boiling, commencing at a temperature of 125° C., by slowly lowering the pressure to about 30 mbar. The colourless crystal slurry obtained was filtered with suction, washed with xylene and dried.

After washing, the crystal slurry was remelted while distilling off xylene, finally in vacuo, as described above in Example 7a and was again crystallized in a crystallization screw.

| Yield: | 88%, based on o-phenylphenol |
|---|---|
| Content of: | |
| ODOP: | 99.9% |
| o-phenylphenol: | 0.01% |

The xylene-containing mother liquor which contained about 11% of the ODOP formed was able to be reused in the next batch. The yield then rose to about 98% of the theoretical yield, based on o-phenylphenol.

EXAMPLE 7c)

A final part of 304 g (corresponding to 1.30 chlorine equivalents) of the distillate from Example 5 was melted in a flask and brought to from 120° to 130° C. While stirring vigorously, an amount of 28.8 g (1.60 mol) of water was blown in as steam through a fret at the bottom of the flask over a period of from 3 to 4 hours.

The stream of hydrogen chloride evolved here was conducted away via a condenser.

After the hydrolysis was complete, there was obtained a slightly yellowish melt which was crystallized.

| Yield: | 275.8 g, namely 98.3% of the theoretical yield, based on o-phenylphenol |
|---|---|
| Hazen colour No.: | 15 (10% strength solution in acetone) |
| Content of: | |
| Chlorine: | 81 ppm |
| ODOP: | 99.8% |
| o-phenylphenol: | 0.01% |

EXAMPLE 8 (comparative)

450 g (3.28 mol) of $PCl_3$ were added dropwise at from 80° to 115° C. to 422 g (2.48 mol) of o-phenylphenol over a period of 3.5 hours, with a vigorous stream of HCl being given off. After a further 3 hours, the internal temperature was 150° C and the evolution of HCl abated. 2.1 g of $ZnCl_2$ were added and the heating was continued for 6 hours up to a temperature of about 200° C. During the entire reaction time, the cooling water temperature fluctuated between about 16 and 19° C. At the end of the reaction time, the excess of $PCl_3$ was 0.04 mol per mol of o-phenylphenol used.

The distillation of the product using a method similar to Example 1 gave a distillation yield of 82%.

After hydrolysis as in Example 6, an ODOP having an o-phenylphenol content of 4.2% was obtained.

What is claimed is:

1. A process for preparing a 6-oxo-(6H)-dibenz-[c,e][1,2]-oxaphosphorin (ODOP) of the formula

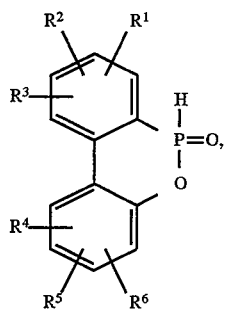

where
$R^1$ to $R^6$ are identical or different and are hydrogen, halogen, $C_1-C_4$-alkyl or $C_1-C_4$-alkoxy by reaction of an o-phenylphenol of the formula

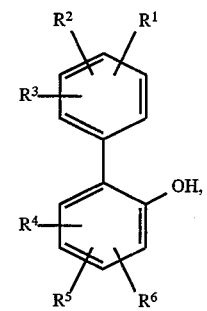

where
$R^1$ to $R^6$ are as defined above,
with phosphorus trichloride in the presence of Lewis acids with elimination of hydrogen chloride at elevated temperature in the range from 70° to 220° C. in a first stage and hydrolysis of the product of the first stage in a second stage, wherein during the entire reaction time of the first stage an amount of unreacted phosphorus trichloride of at least 0.05 mol per mol of the o-phenylphenol used is maintained in the reaction mixture and the product of the first stage is, after removal of the excess $PCl_3$, reacted as melt or dissolved in an inert solvent with from 1.021 to 2 mol of $H_2O$ per chlorine equivalent of the product of the first stage at from 50° to 150° C. and HCl and residual $H_2O$ are removed by heating to from 140° to 170° C.

2. The process of claim 1, wherein the product of the first stage is reacted with from 1.021 to 1.7 mol of $H_2O$ per chlorine equivalent of the product of the first stage.

3. The process of claim 2, wherein the product of the first stage is reacted with from 1 to 1.5 mol of $H_2O$ per chlorine equivalent of the product of the first stage.

4. The process of claim 1 wherein the product of the first stage is reacted with $H_2O$ at from 70° to 130° C.

5. The process of claim 1, wherein the excess $PCl_3$ is removed from the reaction mixture after completion of the first stage by distillation in the presence of an inert solvent having a boiling point higher than that of $PCl_3$ and lower than that of 6-chloro-(6H)-dibenz-[c,e][1,2]-oxaphosphorin.

6. The process of claim 1, wherein two of the radicals $R^1$ to $R^6$ are hydrogen.

7. The process of claim 6, wherein four of the radicals $R^1$ to $R^6$ are hydrogen.

8. The process of claim 7, wherein all the radicals $R^1$ to $R^6$ are hydrogen.

9. The process of claim 1, wherein the reaction is carried out in a first reaction phase of the first stage in the range from 70° to 140° C. without Lewis acids and in a second reaction phase of the first stage in the range from 160° to 220° C. in the presence of Lewis acids.

10. The process of claim 5, wherein solvents having boiling points in the range from 90° to 200° C. are used.

11. The process of claim 10, wherein solvents having boiling points in the range from 100° to 180° C. are used.

12. The process of claim 11, wherein solvents having boiling points in the range from 105° to 170° C. are used.

13. The process of claim 10, wherein a solvent or a mixture of a plurality of solvents selected from the group consisting of methylcyclohexane, isooctane, isodecane, isododecane, isononane, dimethylcyclohexane, benzines such as petroleum ether, dicyclopentane, decalin, toluene, cumene, xylenes, mesitylene, cymenes, chlorobenzene, chlorotoluene, bromobenzene, di- chlorobenzene, chlorocumene, ethylbenzene and diethylbenzene is used.

14. The process of claim 1, wherein the hydrolysis in the second stage is carried out using one of the solvents as are used for the removal of the $PCl_3$ in the first stage.

15. The process of claim 14, wherein the same solvent is used in the first and second stages.

16. The process of claim 15, wherein the solvent used in the first and second stages is xylene.

* * * * *